United States Patent
Wei et al.

(10) Patent No.: US 11,518,728 B2
(45) Date of Patent: *Dec. 6, 2022

(54) MULTI-ARM SINGLE MOLECULAR WEIGHT POLYETHYLENE GLYCOL, ACTIVE DERIVATIVE THEREOF, AND PREPARATION AND APPLICATION THEREOF

(71) Applicant: JENKEM TECHNOLOGY CO., LTD. (TIANJIN), Tianjin (CN)

(72) Inventors: Zhen Wei, Tianjin (CN); Meina Lin, Tianjin (CN); Xuan Zhao, Tianjin (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 233 days.

This patent is subject to a terminal disclaimer.

(21) Appl. No.: 16/729,653

(22) Filed: Dec. 30, 2019

(65) Prior Publication Data

US 2020/0131109 A1    Apr. 30, 2020

Related U.S. Application Data

(63) Continuation of application No. PCT/CN2018/093523, filed on Jun. 29, 2018.

(30) Foreign Application Priority Data

Jun. 30, 2017 (CN) .......................... 201710523405.7
Jun. 22, 2018 (CN) .......................... 201810651779.1

(51) Int. Cl.

| | | |
|---|---|---|
| C07C 31/22 | (2006.01) | |
| C07C 31/24 | (2006.01) | |
| C07C 59/305 | (2006.01) | |
| C07C 59/31 | (2006.01) | |
| A61K 47/60 | (2017.01) | |
| C07C 31/20 | (2006.01) | |
| C07D 303/12 | (2006.01) | |

(52) U.S. Cl.
CPC ............ *C07C 59/305* (2013.01); *A61K 47/60* (2017.08); *C07C 31/202* (2013.01); *C07D 303/12* (2013.01)

(58) Field of Classification Search
CPC ... C07C 31/225; C07C 31/245; C07C 31/202; C07C 59/305; C07C 59/31; A61K 47/60
USPC ................................................. 554/213, 227
See application file for complete search history.

(56) References Cited

U.S. PATENT DOCUMENTS

| | | | |
|---|---|---|---|
| 11,202,796 B2 * | 12/2021 | Wei .......................... A61L 27/52 |
| 2011/0286956 A1 * | 11/2011 | Zhao ................... C08G 65/3344 424/78.3 |
| 2019/0016856 A1 * | 1/2019 | Wei ..................... C08G 65/3344 |

FOREIGN PATENT DOCUMENTS

| | | |
|---|---|---|
| CN | 101724144 A | 6/2010 |
| CN | 102108119 A | 6/2011 |
| CN | 104371098 A | 2/2015 |
| CN | 104479126 A | 4/2015 |
| CN | 104497303 A | 4/2015 |
| CN | 104877127 A | 9/2015 |
| CN | 104981455 A | 10/2015 |
| JP | 2003246835 A | 9/2003 |

OTHER PUBLICATIONS

Daquan Xue, et al., "Application and technology of polyethylene glycol in medical field," Date: Apr. 30, 2011, Relevant pages of the publication: 80, Publisher Huazhong University of Science and Technology Press, Place of publication China.

Hailian Zhang, et al., "Preparation of multi-arm star polyethylene glycol," China Synthetic Resins and Plastics, Date: Dec. 26, 2012, Relevant pages of the publication: 38-40, 54, Volume-issue No. vol. 29(4), Publisher College of Chemistry and Life Sciences, Leshan Normal University, Place of publication: China.

PCT International Search Report for PCT/CN2018/093523, dated Sep. 4, 2018.

Written Opinion of the International Searching Authority for PCT/CN2018/093523, dated Sep. 4, 2018.

* cited by examiner

*Primary Examiner* — Joseph R Kosack
*Assistant Examiner* — Sagar Patel
(74) *Attorney, Agent, or Firm* — Flener IP & Business Law; Zareefa B. Flener

(57) ABSTRACT

Being used for drug modification, the multi-arm single molecular weight polyethylene glycol and an active derivative thereof provided herein can effectively improve the solubility, stability, and immunogenicity of the drugs, improve the absorption of the drugs in vivo, prolong the half-life of the drugs, and increase bioavailability, enhance efficacy, and reduce toxic and side effects of the drugs. A gel formed from the active derivative of the multi-arm single molecular weight polyethylene glycol provided herein can be used for the preparation of controlled release drugs so as to prolong the action time of the drugs, thereby reducing the number of administrations and improving patient compliance.

8 Claims, No Drawings

MULTI-ARM SINGLE MOLECULAR WEIGHT POLYETHYLENE GLYCOL, ACTIVE DERIVATIVE THEREOF, AND PREPARATION AND APPLICATION THEREOF

CROSS-REFERENCE TO RELATED APPLICATION

This application is a continuation application of International patent application No. PCT/CN2018/093523, filed on Jun. 29, 2018, which claims priority to Chinese patent application No. CN201710523405.7, filed on Jun. 30, 2017, and Chinese patent application No. CN201810651779.1, filed on Jun. 22, 2018. All of the aforementioned patent applications are hereby incorporated by reference in their entireties.

FIELD OF THE INVENTION

The invention relates to the technical field of polyethylene glycol functional materials, in particular to a multi-arm single molecular weight polyethylene glycol and active derivative thereof, and preparation and application thereof, in particular, the use in the preparation of a pharmaceutical conjugate, a gel material, a pharmaceutical carrier, and a medical device product.

BACKGROUND OF THE INVENTION

When a functionalized polyethylene glycol is grafted onto a biologically active molecule such as a drug, it may improve the water solubility, biocompatibility and stability of the drug and the like, thereby reducing the toxicity of the drug. Functionalized polyethylene glycols have been widely used in biomedical fields as bioactive molecular modifiers. Although the molecular weight distribution of the currently synthesized polyethylene glycol product is already quite narrow, it is still a mixture of polyethylene glycols with different molecular weights, and the impurities in the mixture often make it difficult to guarantee the repeatability of the biologically active molecule modification process.

In the research and application of bioactive molecules such as drugs, it is a common strategy to avoid the introduction of mixtures. High purity for a final product is one of the main goals. Therefore, it is desirable to prepare high-purity single-molecular weight PEG derivatives for use in medicine and other fields. At present, there are some reports on the application of linear single molecular weight PEG in biomedicine, for example, low molecular weight single molecular weight PEG derivatives as cytotoxin and antibody linkers may be applied to the field of antibody-drug conjugates (ADC).

Compared with a linear PEG product, a multi-arm single-molecular weight PEG product may effectively increase the drug loading per unit; in the meantime, since the terminal position of a multi-arm product may be a heterofunctional group, two or even three drugs can be simultaneously connected in one molecular system, and thus it can be used as a drug for multiple diseases. A multi-arm single-molecular weight PEG product may also be used as a linker in the ADC system, thereby greatly increasing the drug loading of a single ADC molecule. In addition, in the field of medical devices, a multi-arm polyethylene glycol may be used as a crosslinking agent in the production of gels which can be used as binders, penetration inhibitors, anti-blocking agents and hemostatic materials in medical devices. Multi-arm single molecular weight PEG and its derivatives have broad application prospects. However, due to the difficulty in synthesizing the multi-arm single-molecular weight PEG product, the cost of synthesis is high, and it is difficult to perform scale production.

CONTENTS OF THE INVENTION

In order to overcome the deficiencies of the prior art, the inventors of the present invention have devised a multi-arm single molecular weight polyethylene glycol and the active derivative thereof, which may be use for the preparation of a gel, or the preparation of a pharmaceutical conjugate and a pharmaceutical composition by conjugating with a drug molecule.

In one aspect, the invention provides a compound having the following structure:

(I)

wherein A is a core structure, and is a polyol group selected from the group consisting of: residues of pentaerythritol, oligo-pentaerythritol, glycerol and oligoglycerol, and glyceryl ether groups thereof, $X_1$ is a linking group selected from any one or a combination of two or more of the group consisting of: $-(CH_2)_i-$, $-(CH_2)_iO-$, $-(CH_2)_iNHCO-$, $-(CH_2)_iCONH-$, $-(CH_2)_iOCO-$, and $-(CH_2)_iCOO-$, and i is an integer from 1 to 10 (for example, 0, 1, 2, 3, 4, 5, 6, 7, 8, 9, or 10), Y is a terminal group selected from any one of the group consisting of: hydroxyl, carboxyl, ester group, ketone group, amino, mercapto group, maleimide group, alkynyl, and azido, and n is an integer from 3 to 24.

In an embodiment of the invention, the A has the following structure:

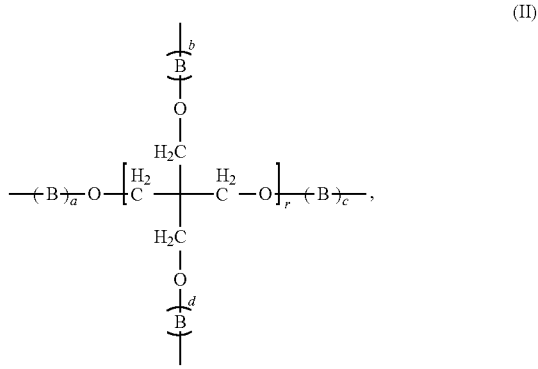

(II)

wherein B has the following structure:

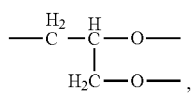

r is an integer from 1 to 5 (for example, 1, 2, 3, 4 or 5),
a, b, c and d are integers and each independently selected from 0 and 1.

In another embodiment of the invention, the A has the following structure:

(III)

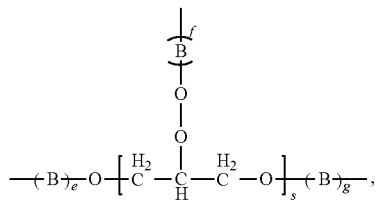

wherein B has the following structure:

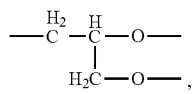

s is an integer from 1 to 5 (for example, 1, 2, 3, 4 or 5), e, f and g are integers and each independently selected from 0 and 1.

In an embodiment of the invention, in formula II, the r is 1, 2 or 3.

In an embodiment of the invention, in formula II, the a, b, c and d are all 0.

In an embodiment of the invention, in formula II, the a, b, c, and d are all 1.

In an embodiment of the invention, in formula III, the s is 1, 2 or 3.

In an embodiment of the invention, in formula III, the e, f, and g are all 0.

In an embodiment of the invention, in formula III, the e, f and g are all 1.

In an embodiment of the invention, the A has the following structure:

(II-1)

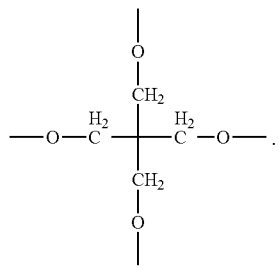

In an embodiment of the invention, the A has the following structure:

(II-2)

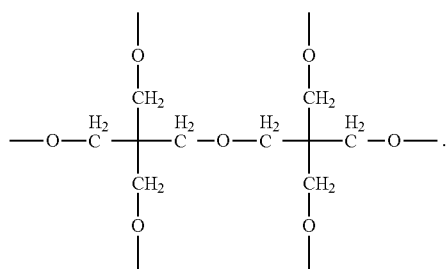

In an embodiment of the invention, the A has the following structure:

(II-3)

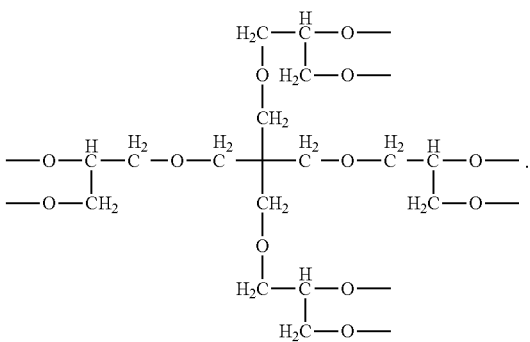

In an embodiment of the invention, the A has the following structure:

(II-4)

In an embodiment of the invention, the A has the following structure:

(III-1)

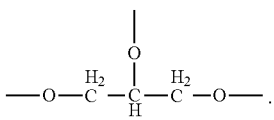

In an embodiment of the invention, the A has the following structure:

(III-2)

In an embodiment of the invention, n is an integer from 3 to 16, for example, 3, 4, 5, 6, 7, 8, 10, 12, 14, or 16.

In an embodiment of the invention, in the $X_1$, the i is an integer of 1-5, for example, 1, 2, 3, 4 or 5, preferably 1, 2 or 3.

In an embodiment of the invention, the $X_1$ is selected from any one or a combination of two or more of the group consisting of: —$CH_2$—, —$CH_2CH_2$—, —$CH_2CH_2CH_2$—, —$CH_2CONHCH_2$—, and —$CH_2CONHCH_2CH_2$—.

In a preferred embodiment of the invention, the $X_1$ is —$CH_2CH_2$—.

In an embodiment of the invention, in the Y, the ester group is selected from any one of the group consisting of:

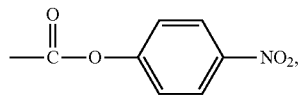

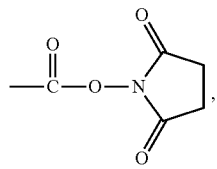

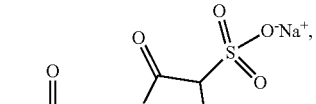

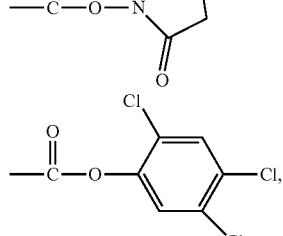

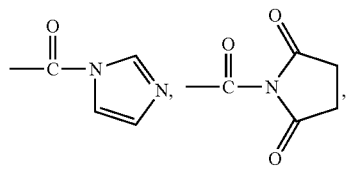

S, and

In an embodiment of the invention, in the Y, the ketone group is selected from any one of the group consisting of:

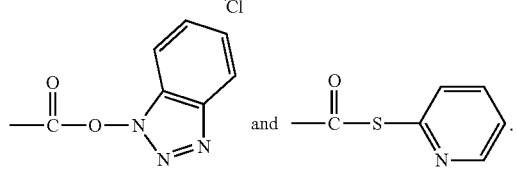

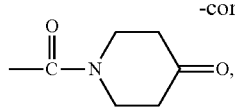

—COCH$_3$ and —COCH$_2$CH$_3$.

In a preferred embodiment of the invention, the Y is —COOH.

In a more preferred embodiment of the invention, the —X$_1$—Y is —CH$_2$CH$_2$COOH.

In an embodiment of the invention, the compound has the following structure:

(I-1)

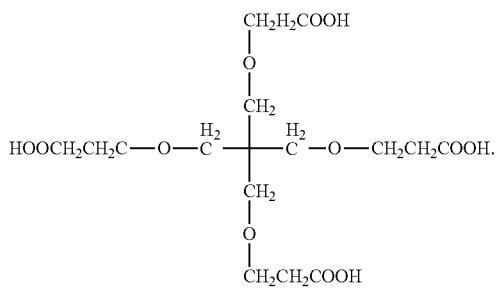

In an embodiment of the invention, the compound has the following structure:

(I-2)

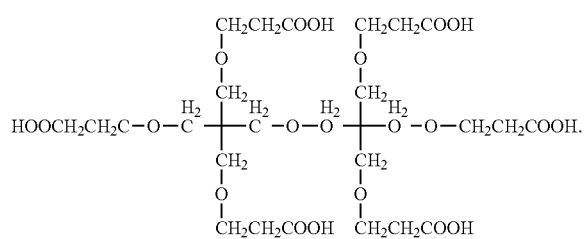

In an embodiment of the invention, the compound has the following structure:

(I-3)

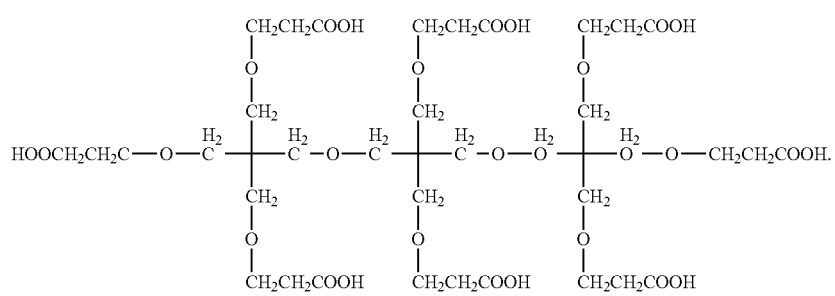

In an embodiment of the invention, the compound has the following structure:

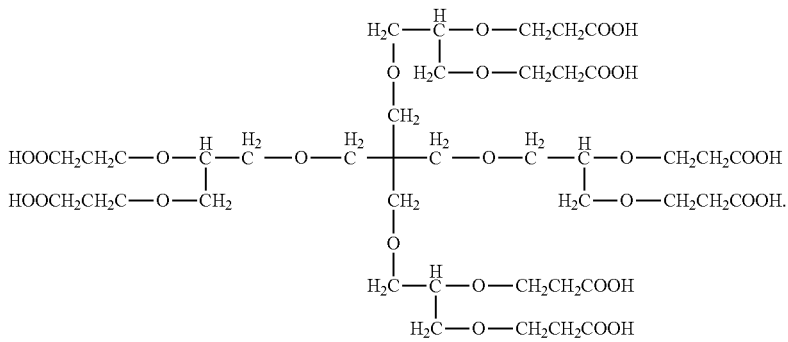

(I-4)

In an embodiment of the invention, the compound has the following structure:

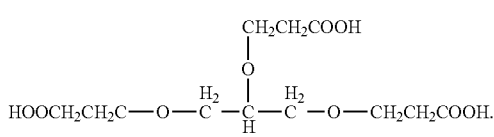

(I-5)

In an embodiment of the invention, the compound has the following structure:

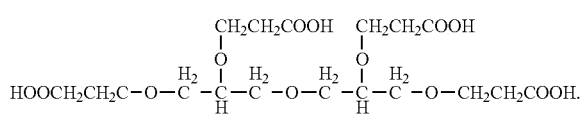

(I-6)

Another aspect of the invention also provides a multi-arm single molecular weight polyethylene glycol having the following structure:

(IV)

wherein A and $X_1$ are defined as above in the invention,
R is a linking group selected from any one or a combination of two or more of the group consisting of: —NHCO—, —CONH—, —OCO—, —COO—, —O—,

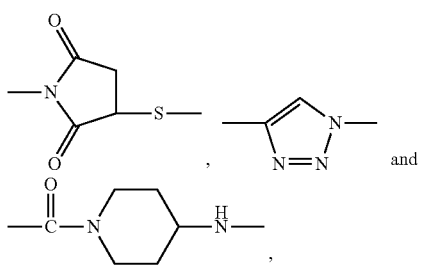

$X_2$ is a linking group selected from any one or a combination of two or more of the group consisting of: —(CH$_2$)$_j$—, —(CH$_2$)$_j$O—, —(CH$_2$)$_j$COO—, —(CH$_2$)$_j$NH—, —(CH$_2$)$_j$NHCO—, —(CH$_2$)$_j$CONH—, —(CH$_2$)$_j$OCO— and —(CH$_2$)$_j$COO—, and j is an integer from 0 to 10, (for example, 0, 1, 2, 3, 4, 5, 6, 7, 8, 9 or 10), PEG has the following structure: —(CH$_2$CH$_2$O)$_m$—, m is an integer from 4 to 200, and
n is an integer from 3 to 24.

In an embodiment of the invention, the R is selected from any one or a combination of two or more of the group consisting of: —NHCO—, —CONH—,

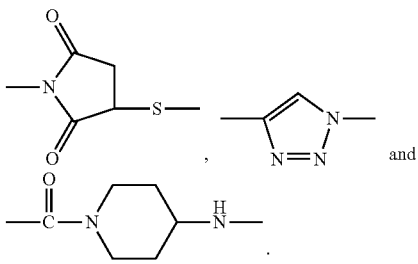

In a preferred embodiment of the invention, the R is —NHCO— or —CONH—.

In an embodiment of the invention, in the $X_2$, the j is an integer from 0 to 5, and for example, may be 0, 1, 2, 3, 4 or 5, preferably 0, 1, 2 or 3.

In an embodiment of the invention, the $X_2$ is selected from any one or a combination of two or more of the group consisting of: a single bond, —CH$_2$—, —CH$_2$CH$_2$—, —CH$_2$CH$_2$CH$_2$—, —CH$_2$CONHCH$_2$— and —CH$_2$CONHCH$_2$CH$_2$—.

In a preferred embodiment of the invention, the $X_2$ is a single bond.

In a specific embodiment of the invention, the —$X_1$—R—$X_2$— is —CH$_2$CH$_2$CONH—.

In the multi-arm single-molecular weight polyethylene glycol according to the present invention, m is an integer from 4 to 200, such as an integer from 4 to 100 (for example, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90 or 100), an integer from 100 to 200 (for example, 100, 110, 120, 130, 140, 150, 160, 170, 180, 190 or 200), preferably an integer from 4 to 100.

In a preferred embodiment of the invention, the m is 4, 12 or 24.

In an embodiment of the invention, the multi-arm single molecular weight polyethylene glycol has the following structure:

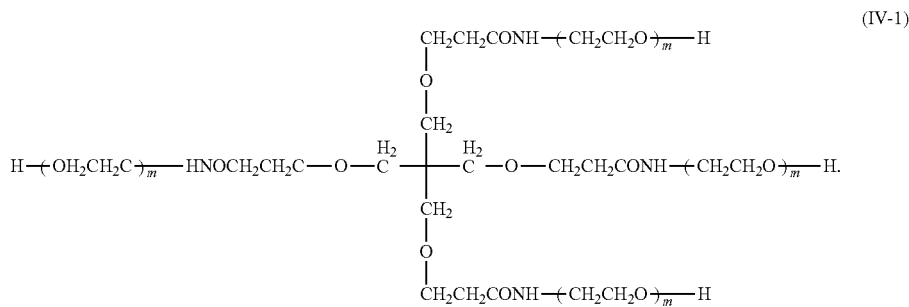
(IV-1)

In an embodiment of the invention, in formula IV-1, m is 4.

In an embodiment of the invention, in formula IV-1, m is 12.

In an embodiment of the invention, in formula IV-1, m is 24.

In an embodiment of the invention, the multi-arm single molecular weight polyethylene glycol has the following structure:

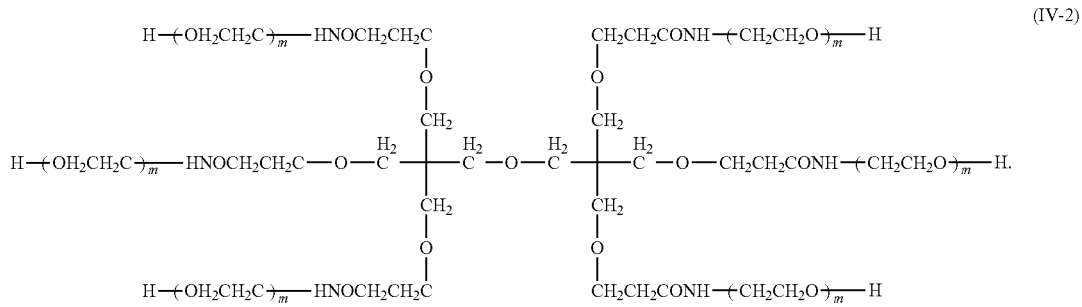
(IV-2)

In an embodiment of the invention, in formula IV-2, m is 4.

In an embodiment of the invention, in formula IV-2, m is 12.

In an embodiment of the invention, in formula IV-2, m is 24.

In an embodiment of the invention, the multi-arm single molecular weight polyethylene glycol has the following structure:

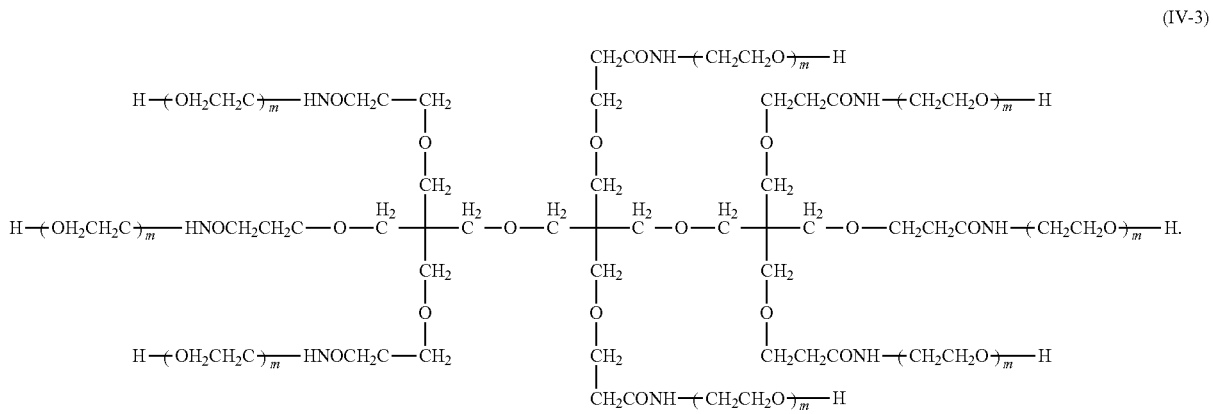
(IV-3)

In an embodiment of the invention, in formula IV-3, m is 4.

In an embodiment of the invention, in formula IV-3, m is 12.

In an embodiment of the invention, in formula IV-3, m is 24.

In an embodiment of the invention, the multi-arm single molecular weight polyethylene glycol has the following structure:

In an embodiment of the invention, in formula IV-6, m is 4.

In an embodiment of the invention, in formula IV-6, m is 12.

In an embodiment of the invention, in formula IV-6, m is 24.

The above compounds of the invention can be used as linkers for the preparation of other multi-arm structures, such as multi-arm polyethylene glycols, particularly the

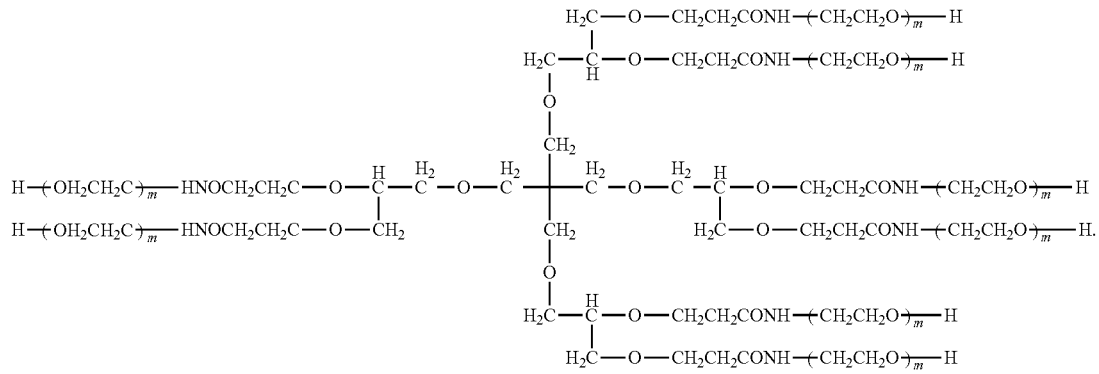

(IV-4)

In an embodiment of the invention, in formula IV-4, m is 4.

In an embodiment of the invention, in formula IV-4, m is 12.

In an embodiment of the invention, in formula IV-4, m is 24.

In an embodiment of the invention, the multi-arm single molecular weight polyethylene glycol has the following structure:

above-described multi-arm single molecular weight polyethylene glycols of the present invention.

Another aspect of the invention provides a method for the preparation of the above-mentioned multi-arm single molecular weight polyethylene glycol, which comprises the step of reacting compound $A\text{--}(X_1\text{--}Y)_n$ described herein with $W\text{--}X_2\text{-PEG-PG}$ to link them together, and the reaction formula is as follows:

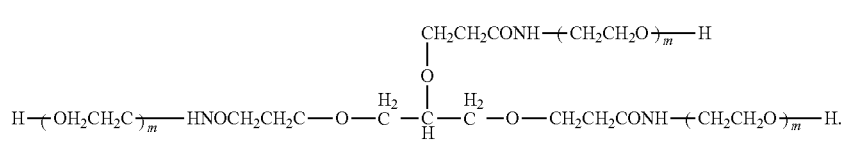

(IV-5)

In an embodiment of the invention, in formula IV-5, m is 4.

In an embodiment of the invention, in formula IV-5, m is 12.

In an embodiment of the invention, in formula IV-5, m is 24.

In an embodiment of the invention, the multi-arm single molecular weight polyethylene glycol has the following structure:

wherein A, $X_1$, Y, $X_2$, n, and PEG are defined as above in the invention,

W is a terminal group selected from any one of the group consisting of: hydroxyl, carboxyl, ester group, ketone group, amino, mercapto group, maleimide group, alkynyl, and azido, and PG is a hydroxyl protecting group.

(IV-6)

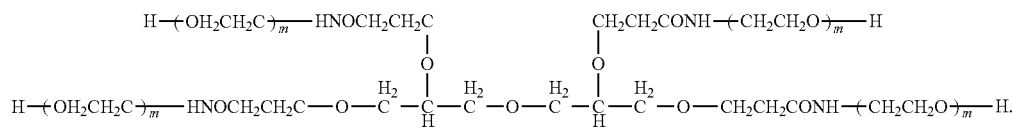

In an embodiment of the invention, the Y is carboxyl, and W is amino; or the Y is amino, and W is carboxyl.

In an embodiment of the invention, the Y is hydroxyl, and W is carboxyl; or the Y is carboxyl, and W is hydroxyl.

In an embodiment of the invention, the Y is ester or ketone group, and W is amino; or the Y is amino, and W is ester or ketone group.

In an embodiment of the invention, the Y is maleimide group, and W is mercapto group; or the Y is mercapto group, and W is maleimide group.

In an embodiment of the invention, the Y is alkynyl, and W is azido; or the Y is azido, and W is alkynyl.

In an embodiment of the invention, the hydroxy protecting group includes, but is not limited to: —CH₃, —C(CH₃)₃, —CH₂OCH₃, —COCH₃, —COC(CH₃)₃, —CH₂CH=CH₂, —Si(CH₃)₃,

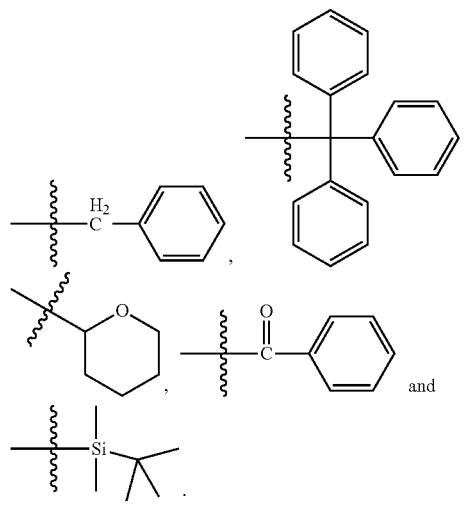

However, those skilled in the art will know that other groups capable of achieving hydroxyl protection can also be used in the above preparation reaction, and the above specific hydroxyl protecting groups are not intended to limit the scope of the present invention.

In an embodiment of the invention, the method further comprises the step of hydroxyl deprotection reaction, and the reaction formula is as follows:

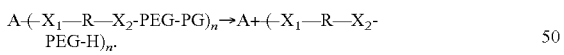

It is known to those skilled in the art that the conventional methods for deprotecting a hydroxyl group in the prior art can be applied to the above reaction, and they are not specifically limited in the present invention.

Another aspect of the invention provides an active derivative of the above multi-arm single molecular weight polyethylene glycol, which has the following structure:

 (V)

wherein the A, $X_1$, R, $X_2$, n, and PEG are defined as above in the invention, F is the same or different —$X_3$—Z type structure, $X_3$ is a linking group selected from any one or a combination of two or more of the group consisting of: —(CH₂)$_k$—, —(CH₂)$_k$O—, —(CH₂)$_k$CO—, —(CH₂)$_k$NH—, —(CH₂)$_k$NHCO—, —(CH₂)$_k$CONH—, —(CH₂)$_k$NHCONH—, —(CH₂)$_k$OCO—, —(CH₂)$_k$COO—, —(CH₂)$_k$OCOO— and —(CH₂)$_k$OCONH—, and k is an integer from 0 to 10, Z is an active terminal group selected from any one of the group consisting of: —H, —NH₂, —ONH₂, —SH, —N₃, —Br, —CONH₂, —CONHNH₂, —COONH₂, —COOH, —PO₃H, —CHO, —CO—HA, —C≡CH,

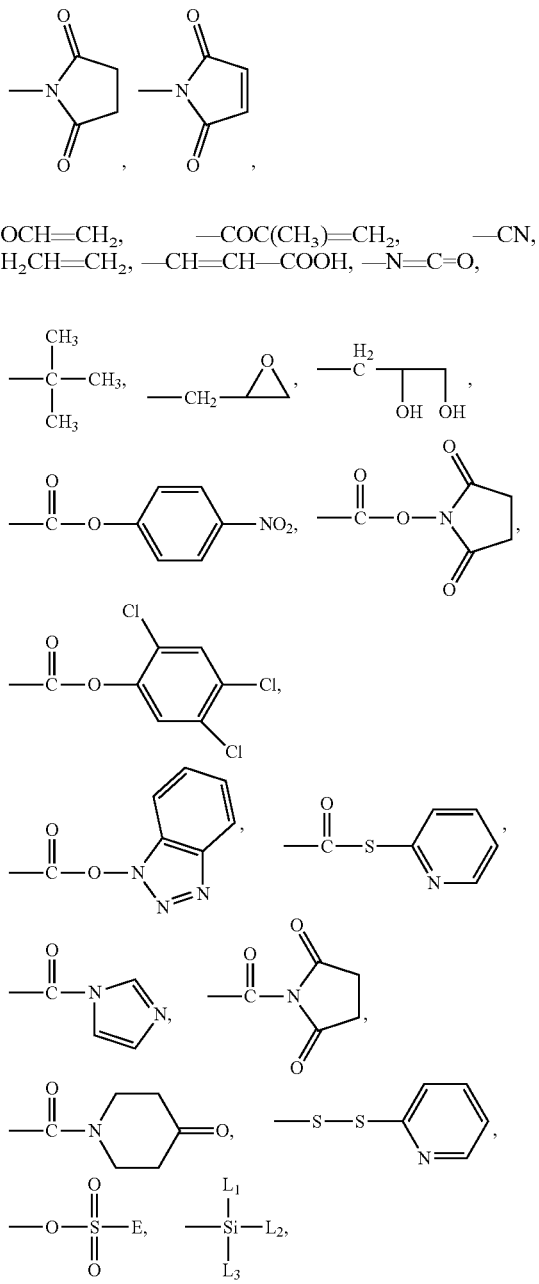

C1-6 alkyl and C1-6 alkoxy,

HA is a halogen atom (for example, —F, —Cl, —Br, or —I),

E is C1-10 hydrocarbyl or fluorine-containing C1-10 hydrocarbyl, $L_{1-3}$ are the same or different C1-10 alkyl or C1-6 alkoxy groups.

In an embodiment of the invention, in the $X_3$, the k is an integer from 1 to 5, for example, 1, 2, 3, 4 or 5, preferably 1, 2 or 3.

In a preferred embodiment of the invention, the $X_3$ is selected from any one or a combination of two or more of the group consisting of: a single bond, —$CH_2$—, —$CH_2CH_2$—, —$CH_2CH_2CH_2$—, —$CH_2O$—, —$CH_2CH_2O$—, —$CH_2CONHCH_2$— and —$CH_2CONHCH_2CH_2$—.

In a preferred embodiment of the invention, the $X_3$ is a single bond or —$CH_2$—.

In an embodiment of the invention, the Z is selected from any one of the group consisting of: —H, —$NH_2$, —SH, —$N_3$, —Br, —$CONH_2$, —COOH, —CHO, —COCl, —COBr, —C≡CH,

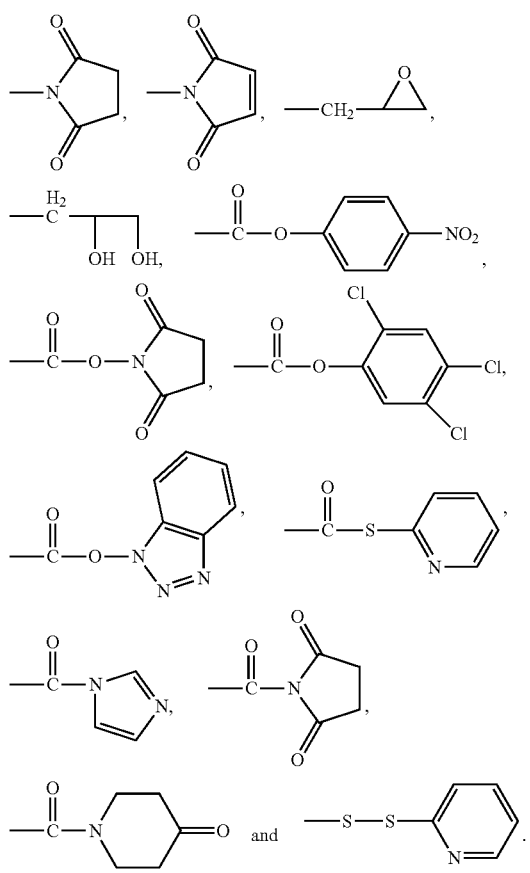

In an embodiment of the invention, in the active derivative, the F is

In another embodiment of the invention, in the active derivative, the F is —H or —$CH_2COOH$.

In an embodiment of the invention, the multi-arm single molecular weight polyethylene glycol active derivative has the following structure:

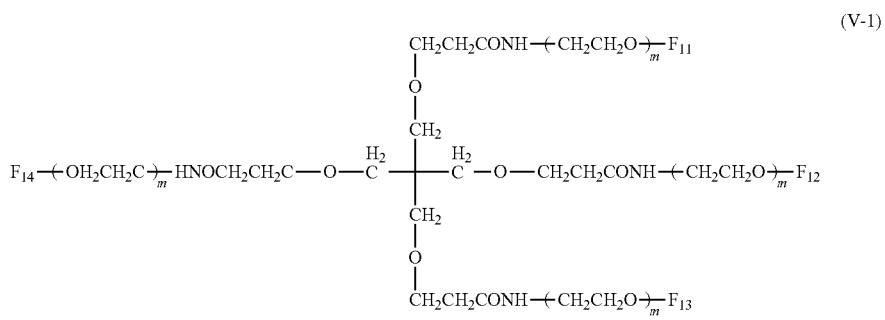

(V-1)

$F_{11-14}$ are the same or different —$X_3$—Z type structures.

In an embodiment of the invention, in formula V-1, m is 4.

In an embodiment of the invention, in formula V-1, m is 12.

In an embodiment of the invention, in formula V-1, m is 24.

In an embodiment of the invention, in formula V-1, $F_{11-14}$ are all

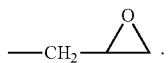

In an embodiment of the invention, in formula V-1, $F_{11-14}$ includes —H and —$CH_2COOH$.

In a preferred embodiment of the invention, in formula V-1, $F_{11-13}$ are all —H, and $F_{14}$ is —$CH_2COOH$.

In another preferred embodiment of the invention, in formula V-1, $F_{11}$ and $F_{12}$ are —H, and $F_{13}$ and $F_{14}$ are —$CH_2COOH$.

In an embodiment of the invention, in formula V-1, $F_{11-14}$ include —H and —$NH_2$.

In a preferred embodiment of the invention, in formula V-1, $F_{11-13}$ are all —H, and $F_{14}$ is —$NH_2$.

In another preferred embodiment of the invention, in formula V-1, $F_{11}$ and $F_{12}$ are —H, and $F_{13}$ and $F_{14}$ are —$NH_2$.

In a more preferred embodiment of the invention, in formula V-1, m is 12, and $F_{11-14}$ are all

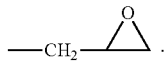

In another more preferred embodiment of the invention, in formula V-1, m is 24, and $F_{11-14}$ are all

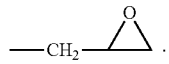

In another more preferred embodiment of the invention, in formula V-1, m is 24, $F_{11-13}$ are all —H, and $F_{14}$ is —CH$_2$COOH.

In another more preferred embodiment of the invention, in formula V-1, m is 24, $F_{11}$ and $F_{12}$ are both —H, and $F_{13}$ and $F_{14}$ are both —CH$_2$COOH.

In an embodiment of the invention, the multi-arm single molecular weight polyethylene glycol active derivative has the following structure:

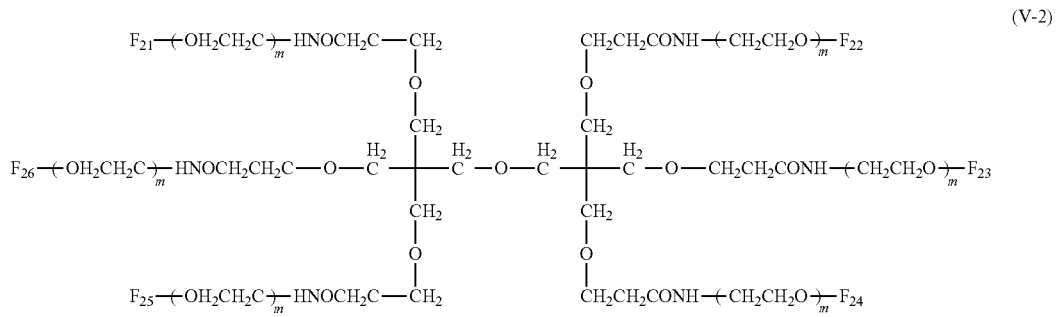

(V-2)

$F_{21-26}$ are the same or different —$X_3$—Z type structures.

In an embodiment of the invention, in formula V-2, m is 4.

In an embodiment of the invention, in formula V-2, m is 12.

In an embodiment of the invention, in formula V-2, m is 24. In an embodiment of the invention, in formula V-2, $F_{21-26}$ are all

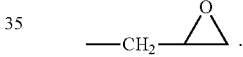

In an embodiment of the invention, in formula V-2, $F_{21-26}$ include —H and —CH$_2$COOH.

In an embodiment of the invention, in formula V-2, $F_{21-25}$ are all —H, and $F_{26}$ is —CH$_2$COOH.

In an embodiment of the invention, in formula V-2, $F_{21-26}$ include —H and —NH$_2$.

In an embodiment of the invention, in formula V-2, $F_{21}$-25 are all —H, and $F_{26}$ is —NH$_2$.

In an embodiment of the invention, the multi-arm single molecular weight polyethylene glycol active derivative has the following structure:

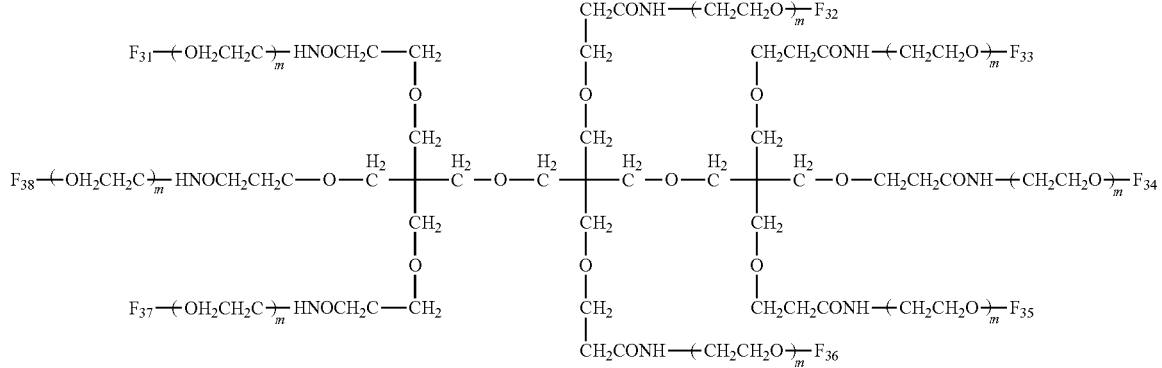

(V-3)

$F_{31-38}$ are the same or different —$X_3$—Z type structures.

In an embodiment of the invention, in formula V-3, m is 4.

In an embodiment of the invention, in formula V-3, m is 12.

In an embodiment of the invention, in formula V-3, m is 24.

In an embodiment of the invention, in formula V-3, $F_{31-38}$ are all

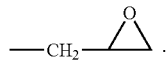

In an embodiment of the invention, in formula V-3, $F_{31-38}$ include —H and —CH$_2$COOH.

In an embodiment of the invention, in formula V-3, $F_{31-37}$ are all —H, and $F_{38}$ is —CH$_2$COOH.

In an embodiment of the invention, in formula V-3, $F_{31-38}$ include —H and —NH$_2$.

In an embodiment of the invention, in formula V-3, $F_{31-37}$ are all —H, and $F_{38}$ is —NH$_2$.

In an embodiment of the invention, the multi-arm single molecular weight polyethylene glycol active derivative has the following structure:

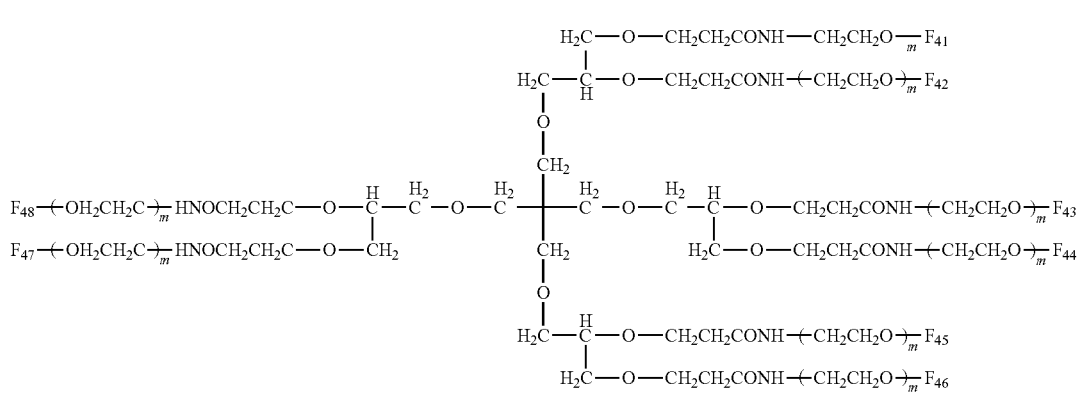

(V-4)

$F_{41-48}$ are the same or different —$X_3$—Z type structures.

In an embodiment of the invention, in formula V-4, m is 4.

In an embodiment of the invention, in formula V-4, m is 12.

In an embodiment of the invention, in formula V-4, m is 24.

In an embodiment of the invention, in formula V-4, $F_{41-48}$ are all

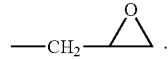

In an embodiment of the invention, in formula V-4, $F_{41-48}$ include —H and —CH$_2$COOH.

In an embodiment of the invention, in formula V-4, $F_{41-47}$ are all —H, and $F_{48}$ is —CH$_2$COOH.

In an embodiment of the invention, in formula V-4, $F_{41-48}$ include —H and —NH$_2$.

In an embodiment of the invention, in formula V-4, $F_{41-47}$ are all —H, and $F_{48}$ is —NH$_2$.

In an embodiment of the invention, the multi-arm single molecular weight polyethylene glycol active derivative has the following structure:

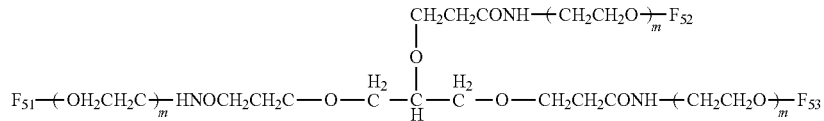

(V-5)

$F_{51-53}$ are the same or different —$X_3$—Z type structures.

In an embodiment of the invention, in formula V-5, m is 4.

In an embodiment of the invention, in formula V-5, m is 12.

In an embodiment of the invention, in formula V-5, m is 24.

In an embodiment of the invention, in formula V-5, $F_{51-53}$ are all

In an embodiment of the invention, the multi-arm single molecular weight polyethylene glycol active derivative has the following structure:

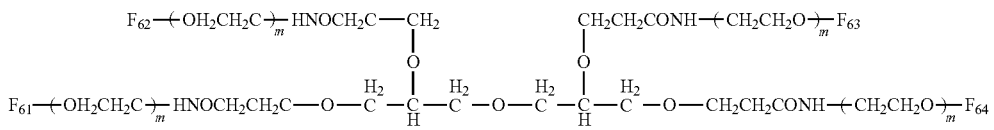 (V-6)

$F_{61-64}$ are the same or different —$X_3$—Z type structures.

In an embodiment of the invention, in formula V-6, m is 4.

In an embodiment of the invention, in formula V-6, m is 12.

In an embodiment of the invention, in formula V-6, m is 24.

In an embodiment of the invention, in formula V-6, $F_{61-64}$ are all

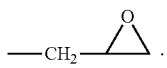

Another aspect of the invention also provides a gel formed from the above multi-arm single molecular weight polyethylene glycol active derivative.

Another aspect of the invention also provides a conjugate of the above multi-arm single molecular weight polyethylene glycol and a drug molecule.

Another aspect of the invention also provides a conjugate of the above multi-arm single molecular weight polyethylene glycol active derivative and a drug molecule.

In an embodiment of the invention, the drug molecule is selected from the group consisting of: amino acids, polypeptides, proteins, nucleosides, carbonhydrates, organic acids, flavonoids, quinones, terpenoids, phenylpropanoids, steroids and their glycosides, and alkaloids, and combinations thereof.

In a specific embodiment of the invention, the drug molecule is selected from one or more of the group consisting of: chlorambucil, cisplatin, 5-fluorouracil, paclitaxel, doxorubicin, methotrexate, irinotecan and docetaxel.

In another embodiment of the invention, the drug molecule is selected from one or more of the group consisting of: interferon, interleukin, tumor necrosis factor, growth factor, colony stimulating factor, erythropoietin, and superoxide dismutase.

In a preferred embodiment of the invention, the drug molecule is docetaxel.

In a preferred embodiment of the invention, the drug molecule is irinotecan.

In a preferred embodiment of the invention, the multi-arm single molecular weight polyethylene glycol active derivative is an eight-arm polyethylene glycol acetate.

In a more preferred embodiment of the invention, the conjugate of the invention is a conjugate of eight-arm polyethylene glycol acetate with irinotecan or docetaxel.

Another aspect of the invention also provides a pharmaceutical composition comprising the above conjugate and a pharmaceutically acceptable additive.

In the pharmaceutical composition, the additive may be any one or more of the group consisting of: excipients, disintegrants, binders, lubricants, suspending agents, stabilizers, fillers, adhensives, and the like. Examples of the excipients include: lactose, mannitol, isomalt, microcrystalline cellulose, silicified microcrystalline cellulose, powdered cellulose, and the like; examples of the disintegrants include low-substituted hydroxypropylcellulose, cross-linked povidones, sodium starch glycolate, cross-linked sodium carboxymethyl cellulose, and starch, etc.; examples of the binders include hydroxypropylcellulose, hypromellose, povidone, copovidone and pregelatinized starch etc.; examples of the lubricants include stearic acid, magnesium stearate, and fumarate sodium stearate, and the like; examples of the wetting agents include polyoxyethylene sorbitan fatty acid ester, poloxamer, and polyoxyethylene castor oil derivatives and the like; examples of the suspending agents include hypromellose, hydroxypropylcellulose, povidone, copovidone, sodium carboxymethylcellulose, methylcellulose, and the like; examples of the stabilizers include citric acid, fumaric acid, succinic acid and the like; examples of the fillers include starch, sucrose, lactose, and microcrystalline cellulose etc.; and examples of the adhensives include cellulose derivatives, alginate, gelatin, and polyvinyl pyrrolidone and the like. Furthermore, the pharmaceutical composition of the invention may further include any one or more of the group consisting of: anti-coagulants, flavor enhancers, emulsifiers, preservatives, and the like.

The pharmaceutical composition of the invention may be tablets (including sugar-coated tables, film-coated tables, sublingual tables, orally disintegrating tables, oral tables, etc.), pills, powders, granules, capsules (including soft capsules and microcapsules, etc.), lozenges, syrups, liquids, emulsions, suspensions, controlled release preparations (for example, transient release preparations, sustained release preparations, and sustained release microcapsules), aerosols, films (for example, oral disintegrating films, oral mucosaadhesive films), injections (for example, subcutaneous injections, intravenous injections, intramuscular injections, and intraperitoneal injections), intravenous drips, transdermal absorption preparations, ointments, lotions, adhesive preparations, suppositories (eg, rectal suppositories and pessaries, etc.), small pills, nasal preparations, pulmonary preparations (inhalations), eye drops, etc., oral or parenteral preparations (eg, administering near the tumor and directly to the lesion by intravenous, intramuscular, subcutaneous, intra-organ, intranasal, intradermal, infusion, intra-cerebral and intra-rectal administration).

Another aspect of the invention also provides the use of the above compound in the preparation of a multi-arm polyethylene glycol, a multi-arm polyethylene glycol active derivative, and a pharmaceutical conjugate thereof, and a pharmaceutical composition.

In an embodiment of the invention, the multi-arm polyethylene glycol is the multi-arm single molecular weight polyethylene glycol of the invention described above.

In an embodiment of the invention, the multi-arm polyethylene glycol active derivative is the multi-arm single molecular weight polyethylene glycol active derivative of the invention described above.

Another aspect of the invention provides the use of the above multi-arm single molecular weight polyethylene glycol in the preparation of a multi-arm polyethylene glycol active derivative, a pharmaceutical conjugate thereof, and a pharmaceutical composition.

Another aspect of the invention also provides the use of the above multi-arm single molecular weight polyethylene glycol active derivative in the preparation of a gel, a pharmaceutical conjugate and a pharmaceutical composition.

Another aspect of the invention also provides the use of the above gel in the preparation of a pharmaceutical carrier, and a medical device product.

In an embodiment of the invention, the medical device product is selected from one or more of the group consisting of: a binder, an anti-penetrant, an anti-blocking agent, and a hemostatic material.

Another aspect of the invention provides the use of the above multi-arm single molecular weight polyethylene glycol, the multi-arm single molecular weight polyethylene glycol active derivative, and the pharmaceutical combination thereof, the pharmaceutical composition, and the gel in the preparation of a medicine for preventing and/or treating diseases.

The multi-arm single molecular weight polyethylene glycol and the active derivative thereof provided herein are single molecular weight compounds, thereby avoiding the application of high molecular polymer mixture in the prior art, and effectively improving the purity of the drugs. Being used for drug modification, the multi-arm single molecular weight polyethylene glycol and an active derivative thereof provided herein can effectively improve the solubility, stability, and immunogenicity of the drugs, improve the absorption of the drugs in vivo, prolong the half-life of the drugs, and increase bioavailability, enhance efficacy, and reduce toxic and side effects of the drugs. A gel formed from the active derivative of the multi-arm single molecular weight polyethylene glycol provided herein can be used for the preparation of controlled release drugs so as to prolong the action time of the drugs, thereby reducing the number of administrations and improving patient compliance.

SPECIFIC EMBODIMENTS

In the present invention, the term "protecting group" means a substituent which is generally used to block or protect a specific functional group when other functional groups of the compound react. For example, "hydroxy protecting group" refers to a substituent attached to a hydroxyl group that blocks or protects a hydroxyl functional group. Commonly used hydroxyl protecting groups include acetyl, trialkylsilyl, and the like. For general description of protecting groups and their uses, see T. W. Greene, Protective Groups in Organic Synthesis, John Wiley & Sons, New York, 1991.

The term "pharmaceutically acceptable" means a drug is physiologically compatible after administration to a human, and does not cause gastrointestinal disorders, allergic reactions such as dizziness, or the likes.

The term "prevention/preventing" or "treatment/treating" includes therapeutic or prophylactic treatment or measures with the goal of preventing or ameliorating a targeted pathological condition or disorder. The disease of a subject is successfully "prevented" or "treated" if, after receiving a therapeutic amount of the fusion protein of the invention according to the method of the invention, the subject exhibits an observable and/or measurable decrease or disappearance of one or more signs and symptoms of a particular disease.

The technical solutions of the present invention will be described clearly and completely below accompanying with the Examples of the invention. It is obvious that the described embodiments are only part of the embodiments of the invention, and not all of them. All other embodiments obtained by those skilled in the art based on the embodiments of the invention without creative efforts are within the scope of the present invention.

The compounds used in the invention are either commercially available or can be prepared according to the disclosed preparation methods, and they do not limit the therapeutic range of the invention.

Example 1: Synthesis of Tetraacrylic Acid Substituted Pentaerythritol

The tetraacrylic acid substituted pentaerythritol having the following structure (Ia) was synthesized:

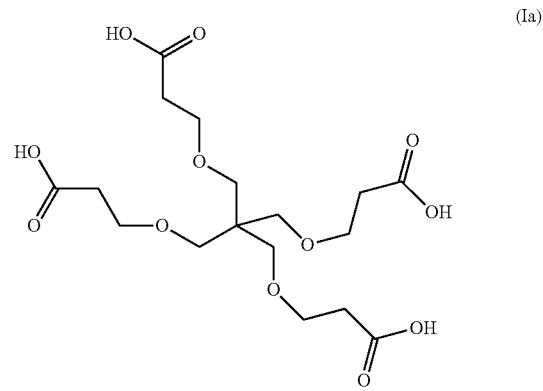 [SMILES: O=C(O)CCOCC(COCCC(=O)O)(COCCC(=O)O)COCCC(=O)O]

(Ia)

Pentaerythritol (1 mol), potassium t-butoxide (0.01 mol), and DMF were added to a three-necked flask, and the mixture was stirred. Then, tert-butyl acrylate (5 mol) was added dropwise to the reaction solution to react at room temperature overnight. After the completion of the reaction, the mixture was filtered, then the reaction mixture was spin-dried, and a silica gel column was used to obtain a pure product of tert-butyl tetraacrylate substituted pentaerythritol.

The pure product of tert-butyl tetraacrylate substituted pentaerythritol was dissolved in a dichloromethane solution containing 50% TFA, reacting at room temperature overnight. After the completion of the reaction, the reaction solution was spin-dried, and then acetonitrile was recrystallized to obtain a pure product of tetraacrylic acid substituted pentaerythritol.

$^1$H-NMR (DMSO-$d_6$): 2.32-2.36 (t, 8H), 3.20 (s, 8H), 3.50-3.54 (t, 8H).

Example 2: Synthesis of Octaacrylic Acid Substituted Pentaerythritol Tetraglyceryl Ether The octaacrylic acid substituted pentaerythritol tetraglyceryl ether having the following structure (Ib) was synthesized:

(Ib)

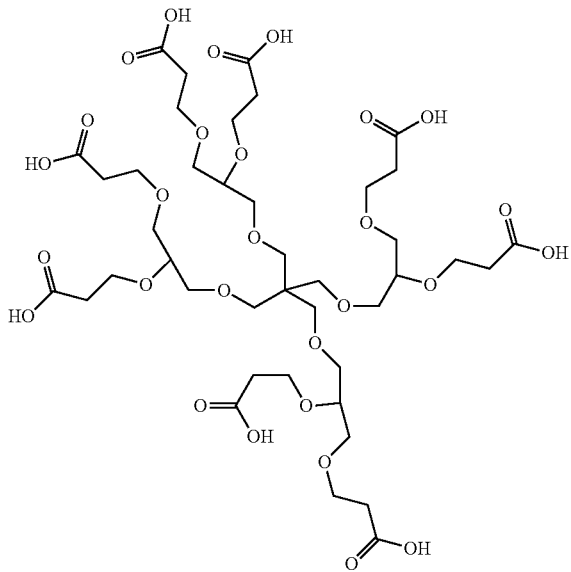

Pentaerythritol tetraglyceryl ether (1 mol), potassium t-butoxide (0.01 mol), and DMF were added to a three-necked flask, and the mixture was stirred. Then, tert-butyl acrylate (10 mol) was added dropwise to the reaction solution to react at room temperature overnight. After the completion of the reaction, the mixture was filtered, then the reaction mixture was spin-dried, and a silica gel column was used to obtain a pure product of tert-butyl octaacrylate substituted pentaerythritol glycerol ether.

The pure product of tert-butyl octaacrylate substituted pentaerythritol glyceryl ether was dissolved in a dichloromethane solution containing 50% TFA, reacting at room temperature overnight. After the completion of the reaction, the reaction solution was spin-dried, and then acetonitrile was recrystallized to obtain a pure product of octaacrylic acid substituted pentaerythritol glyceryl ether.

$^1$H-NMR (DMSO-$d_6$): 2.39-2.45 (m, 16H), 3.29-3.40 (m, 24H), 3.51-3.55 (m, 4H), 3.57-3.61 (m, 8H), 3.67-3.72 (m, 8H); MALDI-TOF (1031.0, M+Na).

Example 3: Synthesis of 4ARM-(EG$_{24}$-OH)$_4$

The 4ARM-(EG$_{24}$-OH)$_4$ having following structure (IIa) was synthesized:

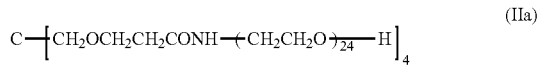

(IIa)

Tetraacrylic acid substituted pentaerythritol (Ia, 1 mol, prepared in Example 1) and NHS (4.4 mol) were added to a three-necked bottle, and then dissolved by stirring with DMF, and DCC (5.2 mol) was added to react at room temperature overnight to obtain a reaction solution 1; then NH$_2$(CH$_2$CH$_2$O)$_{24}$Tr (4.8 mol) and triethylamine (5.2 mol) were dissolved in DMF to obtain a reaction solution 2. Finally, the reaction solution 1 was added dropwise to the reaction solution 2, and the reaction was terminated after reacting at room temperature for 24 hours. After the reaction, the mixture was filtered, and the filtrate was spin-dried, and then a silica gel column was used to obtain a pure product of 4ARM-(EG$_{24}$-OTr)$_4$.

The pure product of 4ARM-(EG$_{24}$-OTr)$_4$ was dissolved in a dichloromethane solution containing 8% TFA, reacting at room temperature overnight. An appropriate amount of 0.1 g/ml sodium hydroxide solution was added under ice bath, reacting at room temperature for 3 hours. After the reaction, the pH of the reaction solution was adjusted to 6.5-7 with 1N hydrochloric acid, then an appropriate amount of sodium chloride was added, and the mixture was extracted twice with dichloromethane, and the dichloromethane phase was spin-dried; and then an appropriate amount of water was added to dissolve the spin dried substance of the dichloromethane phase. Then the mixture was filtered, and the filtrate was again collected and spin-dried to give a product of 4ARM-(EG$_{24}$-OH)$_4$.

$^1$H-NMR (DMSO-$d_6$): 2.26-2.30 (m, 8H), 3.17-3.21 (m, 16H), 3.35-3.64 (m, 384H), 4.58-4.62 (t, 4H), 7.90-7.94 (t, 4H);
MALDI-TOF (4671.5, M+Na).

Example 4: Synthesis of 4ARM-(EG$_{12}$-OH)$_4$

The 4ARM-(EG$_{12}$-OH)$_4$ having the following structure (IIb) was synthesized:

(IIb)

Tetraacrylic acid substituted pentaerythritol (Ia, 1 mol, prepared in Example 1) and NHS (4.4 mol) were added to a three-necked bottle, and then dissolved by stirring with DMF, and DCC (5.2 mol) was added to react at room temperature overnight to obtain a reaction solution 1; then NH$_2$(CH$_2$CH$_2$O)$_{12}$Tr (4.8 mol) and triethylamine (5.2 mol) were dissolved in DMF to obtain a reaction solution 2. Finally, the reaction solution 1 was added dropwise to the reaction solution 2, and the reaction was terminated after reacting at room temperature for 24 hours. After the reaction, the mixture was filtered, and the filtrate was spin-dried, and then a silica gel column was used to obtain a pure product of 4ARM-(EG$_{12}$-OTr)$_4$.

The pure product of 4ARM-(EG$_{12}$-OTr)$_4$ was dissolved in a dichloromethane solution containing 8% TFA, reacting at room temperature overnight. An appropriate amount of 0.1 g/ml sodium hydroxide solution was added under ice bath, reacting at room temperature for 3 hours. After the reaction, the pH of the reaction solution was adjusted to 6.5-7 with 1N hydrochloric acid, then an appropriate amount of sodium chloride was added, and the mixture was extracted twice with dichloromethane, and the dichloromethane phase was spin-dried; and then an appropriate amount of water was added to dissolve the spin dried substance of the dichloromethane phase. Then the mixture was filtered, and the filtrate was again collected and spin-dried to give a product of 4ARM-(EG$_{12}$-OH)$_4$.

$^1$H-NMR (DMSO-$d_6$): 2.26-2.30 (m, 8H), 3.17-3.21 (m, 16H), 3.35-3.64 (m, 192H), 4.56-4.59 (t, 4H), 7.88-7.92 (t, 4H);
MALDI-TOF (2557.6, M+Na).

Example 5: Synthesis of 8ARM-(EG$_4$-OH)$_8$

The 8ARM-(EG$_4$-OH)$_8$ having the following structure 8 (IIc) was synthesized:

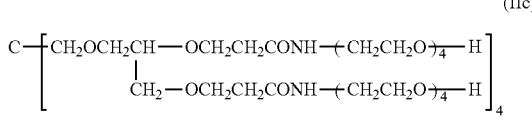

(IIc)

Octaacrylic acid substituted pentaerythritol tetraglyceryl ether (Ib, 1 mol, prepared in Example 2) and NHS (8.8 mol) were added to a three-necked bottle, and then dissolved by stirring with DMF, and DCC (10.4 mol) was added to react at room temperature overnight to obtain a reaction solution 1; then $NH_2(CH_2CH_2O)_4Tr$ (9.6 mol) and triethylamine (10.4 mol) were dissolved in DMF to obtain a reaction solution 2. Finally, the reaction solution 1 was added dropwise to the reaction solution 2, and the reaction was terminated after reacting at room temperature for 24 hours. After the reaction, the mixture was filtered, and the filtrate was spin-dried, and then a silica gel column was used to obtain a pure product of 8ARM-$(EG_4$-$OTr)_4$.

The pure product of 8ARM-$(EG_4$-$OTr)_4$ was dissolved in a dichloromethane solution containing 8% TFA, reacting at room temperature overnight. An appropriate amount of 0.1 g/ml sodium hydroxide solution was added under ice bath, reacting at room temperature for 3 hours. After the reaction, the pH of the reaction solution was adjusted to 6.5-7 with 1N hydrochloric acid, then an appropriate amount of sodium chloride was added, and the mixture was extracted twice with dichloromethane, and the dichloromethane phase was spin-dried; and then an appropriate amount of water was added to dissolve the spin dried substance of the dichloromethane phase. Then the mixture was filtered, and the filtrate was again collected and spin-dried to give a product of 8ARM-$(EG_4$-$OH)_4$.

$^1$H-NMR (DMSO-$d_6$): 2.27-2.33 (m, 16H), 3.16-3.20 (m, 16H), 3.28-3.44 (m, 24H), 3.48-3.50 (m, 116H), 3.55-3.60 (m, 8H), 3.66-3.70 (m, 8H), 4.56-4.59 (t, 8H), 7.87-7.90 (t, 8H);

MALDI-TOF (2433.4, M+Na).

Example 6: Synthesis of Four-Arm Dodecaethylene Glycol Tetraglycidyl Ether (IIIa)

The four-arm dodecaethylene glycol tetraglycidyl ether having the following structure (IIIa) was synthesized:

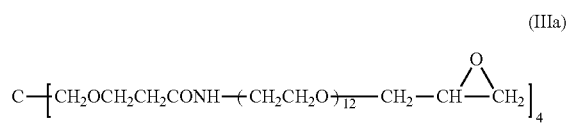

(IIIa)

4ARM-$(EG_{12}$-$OH)_4$ (0.1 mol, prepared in Example 4), tetrahydrofuran (100 mL) and potassium hydroxide (0.8 mol) were added to a three-necked flask, stirring in a water bath; then epichlorohydrin (ECH, 1.2 mol) was added dropwise to the reaction system, and the reaction temperature was controlled to not exceed 35° C., reacting at room temperature overnight. After the reaction, the reaction solution was filtered, and the residue was washed with dichloromethane. Then the filtrate was collected, and a crude product was obtained by removing the dichloromethane through rotary evaporation. The crude product was purified by a silica gel column to obtain a pure product of dodecaethylene glycol tetraglycidyl ether.

$^1$H-NMR (DMSO-$d_6$): 2.26-2.30 (m, 8H), 2.54-2.55 (m, 4H), 2.72-2.73 (m, 4H), 3.09-3.10 (m, 4H), 3.17-3.28 (m, 20H), 3.35-3.64 (m, 192H), 3.70-3.71 (m, 4H), 7.88-7.92 (t, 4H);

MALDI-TOF (2780.3, M+Na).

Example 7: Synthesis of Four-Arm Tetracosethylene Glycol Tetraglycidyl Ether (IIIb)

The four-arm tetracosethylene glycol tetraglycidyl ether having the following structure (IIIb) was synthesized:

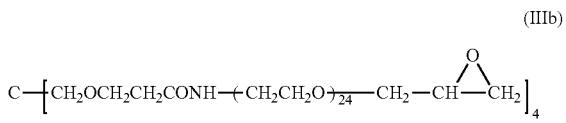

(IIIb)

4ARM-$(EG_{24}$-$OH)_4$ (0.1 mol, prepared in Example 3), tetrahydrofuran (100 mL) and potassium hydroxide (0.8 mol) were added to a three-necked flask, stirring in a water bath; then epichlorohydrin (ECH, 1.2 mol) was added dropwise to the reaction system, and the reaction temperature was controlled to not exceed 35° C., reacting at room temperature overnight. After the reaction, the reaction solution was filtered, and the residue was washed with dichloromethane. Then the filtrate was collected, and a crude product was obtained by removing the dichloromethane through rotary evaporation. The crude product was purified by a silica gel column to obtain a pure product of tetracosethylene glycol tetraglycidyl ether.

$^1$H-NMR (DMSO-$d_6$): 2.26-2.30 (m, 8H), 2.54-2.55 (m, 4H), 2.72-2.73 (m, 4H), 3.09-3.10 (m, 4H), 3.17-3.28 (m, 20H), 3.35-3.64 (m, 384H), 3.70-3.71 (m, 4H), 7.88-7.92 (t, 4H);

MALDI-TOF (4665.9, M+Na).

Example 8: Synthesis of Eight-Arm Tetraethylene Glycol Octaglycidyl Ether (IIIc)

The eight-arm tetraethylene glycol octaglycidyl ether having the following structure (IIIc) was synthesized:

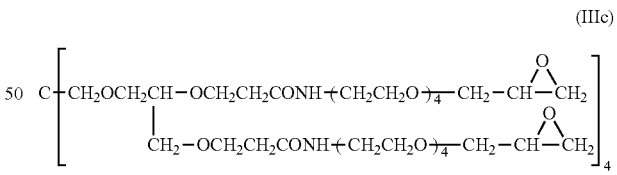

(IIIc)

8ARM-$(EG_4$-$OH)_8$ (0.1 mol, prepared in Example 5), tetrahydrofuran (100 mL) and potassium hydroxide (1.6 mol) were added to a three-necked flask, stirring in a water bath; then epichlorohydrin (ECH, 2.4 mol) was added dropwise to the reaction system, and the reaction temperature was controlled to not exceed 35° C., reacting at room temperature overnight. After the reaction, the reaction solution was filtered, and the residue was washed with dichloromethane. Then the filtrate was collected, and a crude product was obtained by removing the dichloromethane through rotary evaporation. The crude product was purified by a silica gel column to obtain a pure product of eight-arm tetraethylene glycol octaglycidyl ether.

$^1$H-NMR (DMSO-d$_6$): 2.27-2.33 (m, 16H), 2.54-2.55 (m, 8H), 2.72-2.73 (m, 8H), 3.09-3.10 (m, 8H), 3.16-3.26 (m, 24H), 3.28-3.44 (m, 24H), 3.48-3.50 (m, 116H), 3.55-3.60 (m, 8H), 3.66-3.71 (m, 16H), 7.87-7.90 (t, 8H);

MALDI-TOF (2880.8, M+Na).

Example 9: Synthesis of Four-Arm Tetracosethylene Glycol-Monoacetic Acid (IIId) and Four-Arm Tetracosethylene Glycol-Diacetic Acid (IIIe)

The four-arm tetracosethylene glycol-monoacetic acid having the following structure (IIId) was synthesized:

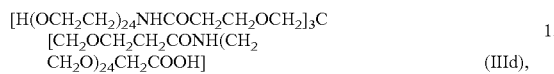

(IIId), and four-arm tetracosethylene glycol-diacetic acid having the following structure (IIIe) was synthesized:

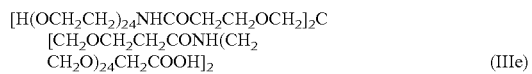

(IIIe)

4ARM-(EG$_{24}$-OH)$_4$ (prepared in Example 3) was taken to remove water with toluene, then distilling off the remaining toluene; tetrahydrofuran and potassium t-butoxide was added to react at room temperature for 2 hours, and t-butyl bromoacetate was added dropwise to react at room temperature overnight, filtering the mixture, and concentrating the filtrate through rotary evaporation. Then NaOH solution (1 mol/L) was added for alkaline hydrolysis at 80° C. for 2 hours, adjusting the pH to 2-3 with 2N hydrochloric acid, then adding NaCl and extracting three times with dichloromethane. The organic phases were combined and dried over anhydrous sodium sulfate, the mixture was filtered, and the filtrate was concentrated through rotary evaporation. The crude product was separated by DEAE anion exchange resin column, and different fractions were respectively collected to obtain a fraction of four-arm tetracosethylene glycol-monoacetic acid and a fraction of four-arm tetracosethylene glycol-diacetic acid. The structures of the products were determined by $^1$H-NMR.

IIId: $^1$H-NMR (DMSO-d$_6$): 2.26-2.30 (m, 8H), 3.17-3.21 (m, 16H), 3.35-3.64 (m, 384H), 4.01 (s, 2H), 4.58-4.62 (t, 3H), 7.90-7.94 (t, 4H);

MALDI-TOF (4729.4, M+Na).

IIIe: $^1$H-NMR (DMSO-d$_6$): 2.27-2.30 (m, 8H), 3.17-3.20 (m, 16H), 3.36-3.64 (m, 384H), 4.02 (s, 4H), 4.59-4.62 (t, 2H), 7.92-7.94 (t, 4H);

MALDI-TOF (4787.5, M+Na).

The above are only the preferred examples of the invention, and are not intended to limit the present invention. Any modifications, equivalent substitutions, etc. within the spirit and principles of the invention, should be included in the scope of the invention.

The invention claimed is:

1. A multi-arm single molecular weight polyethylene glycol having the following structure:

(IV)

wherein A is a core structure, and is a polyol group selected from the group consisting of: residues of pentaerythritol, oligo-pentaerythritol, glycerol and oligoglycerol, and glyceryl ether groups thereof, X$_1$ is a linking group selected from any one or a combination of two or more of the group consisting of: —(CH$_2$)$_i$—, —(CH$_2$)$_i$O—, —(CH$_2$)$_i$NHCO—, —(CH$_2$)$_i$CONH—, —(CH$_2$)$_i$OCO—, and —(CH$_2$)$_i$COO—, and i is an integer from 1 to 10, R is a linking group selected from any one or a combination of two or more of the group consisting of: —NHCO—, —CONH—, —OCO—, —COO—, —O—,

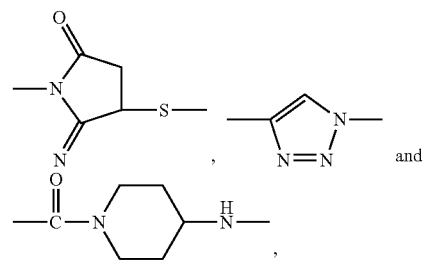

X$_2$ is a linking group selected from any one or a combination of two or more of the group consisting of: —(CH$_2$)$_j$—, —(CH$_2$)$_j$O—, —(CH$_2$)$_j$CO—, —(CH$_2$)$_j$NH—, —(CH$_2$)$_j$NHCO—, —(CH$_2$)$_j$CONH—, —(CH$_2$)$_j$OCO— and —(CH$_2$)$_j$COO—, and j is an integer from 0 to 10, and X$_1$—R—X$_2$— is not —CH$_2$CH$_2$O—, PEG has the following structure: —(CH$_2$CH$_2$O)$_m$—, m is an integer from 4 to 200, and n is an integer from 3 to 24.

2. The multi-arm single molecular weight polyethylene glycol according to claim 1, wherein the A has the following structure:

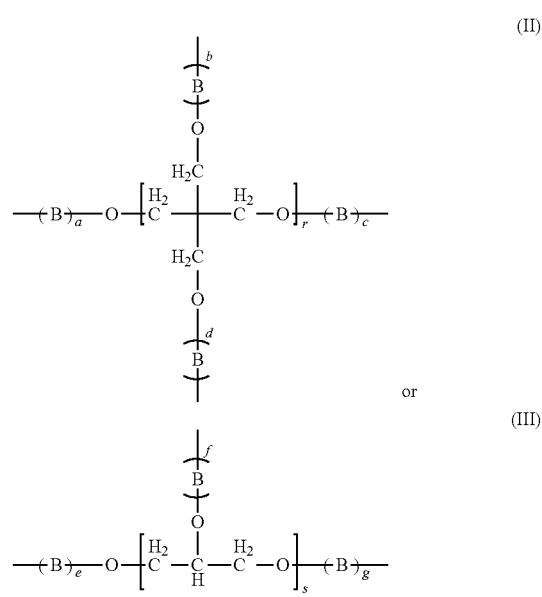

wherein B has the following structure:

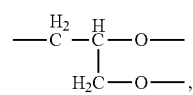

r is an integer from 1 to 5, a, b, c and d are integers and each independently selected from 0 and 1, s is an integer from 1 to 5, e, f and g are integers and each independently selected from 0 and 1.

3. The multi-arm single molecular weight polyethylene glycol according to claim 1, wherein the A is selected from the following structures:

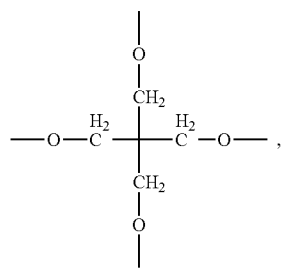
(II-1)

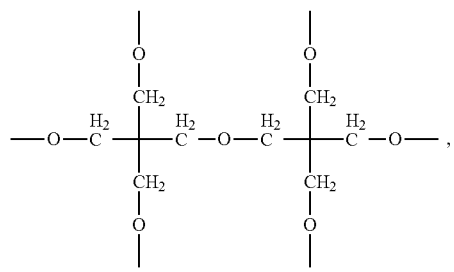
(II-2)

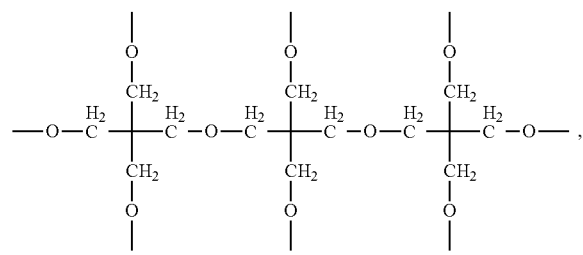
(II-3)

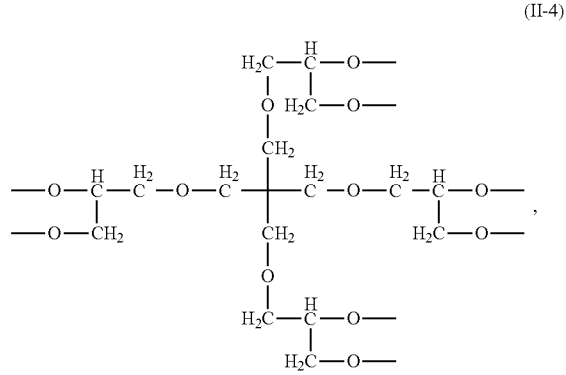
(II-4)

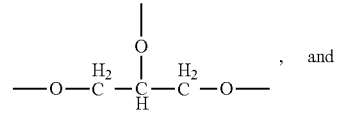
(III-1)
and

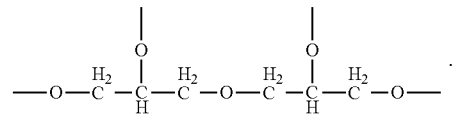
(III-2)

4. The multi-arm single molecular weight polyethylene glycol according to claim 1, wherein the $X_1$ is selected from any one or a combination of two or more of the group consisting of: —$CH_2$—, —$CH_2CH_2$—, —$CH_2CH_2CH_2$—, —$CH_2CONHCH_2$— and —$CH_2CONHCH_2CH_2$—; and/or the R is selected from any one or a combination of two or more of the group consisting of: —NHCO—, —CONH—,

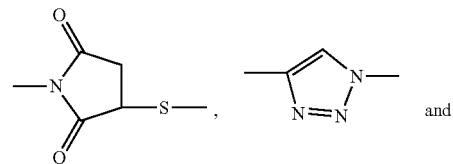

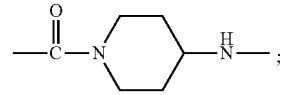;

and/or the $X_2$ is selected from any one or a combination of two or more of the group consisting of: a single bond, —$CH_2$—, —$CH_2CH_2$—, —$CH_2CH_2CH_2$—, —$CH_2CONHCH_2$— and —$CH_2CONHCH_2CH_2$—; and/or the m is an integer from 4 to 100.

5. The multi-arm single molecular weight polyethylene glycol according to claim 4, wherein the multi-arm single molecular weight polyethylene glycol is selected from the following structures:

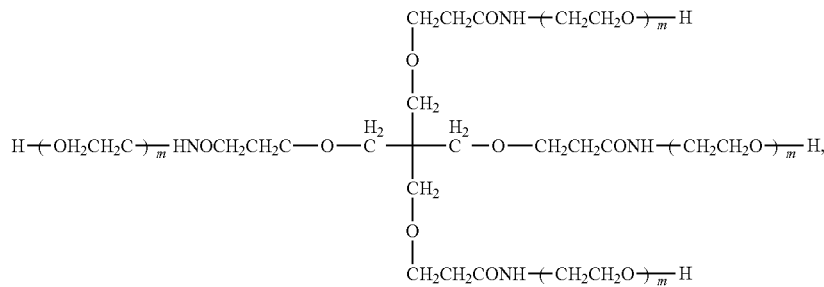
(IV-1)
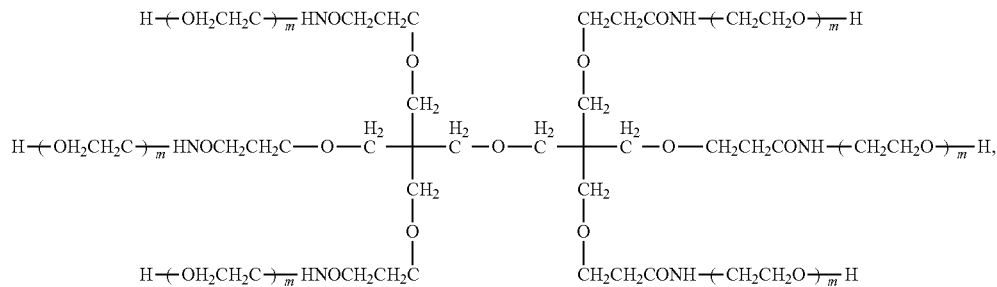
(IV-2)
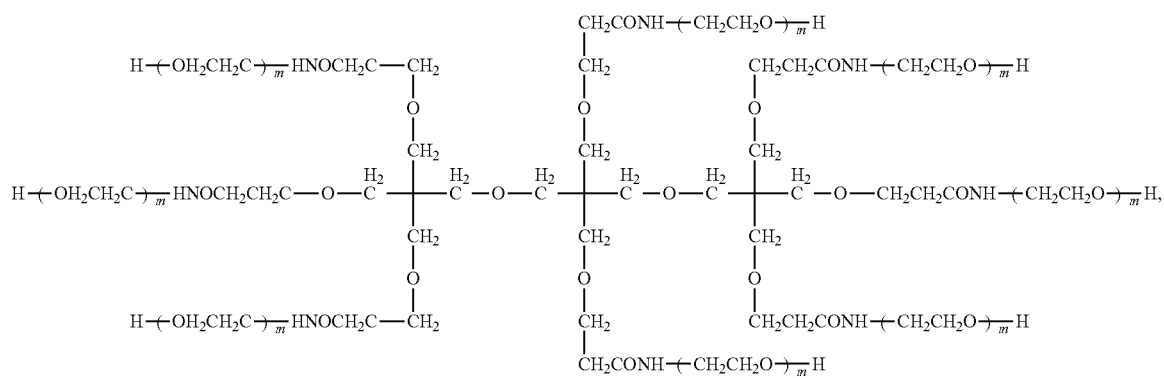
(IV-3)
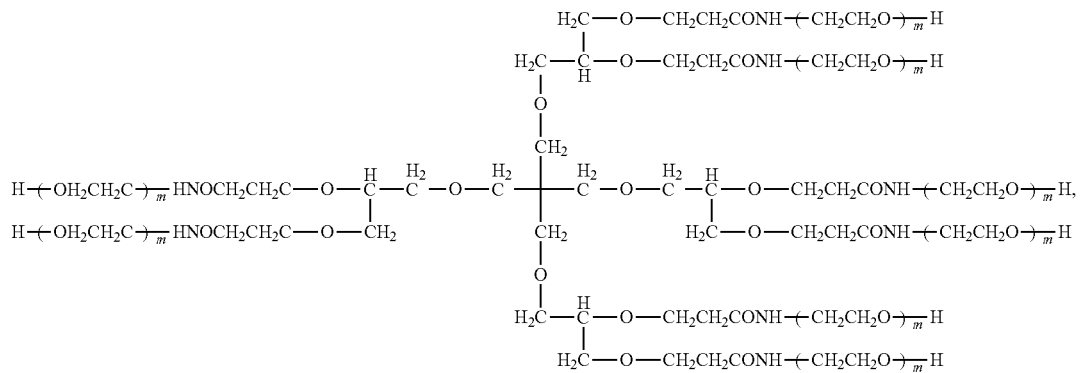
(IV-4)
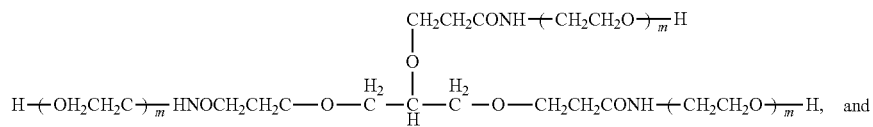
(IV-5)

-continued

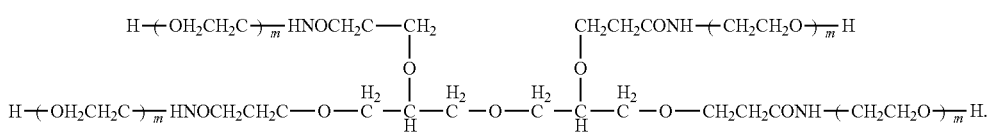

(IV-6)

6. A conjugate of the multi-arm single molecular weight polyethylene glycol according to claim 2 or the active derivative thereof and a drug molecule.

7. A pharmaceutical composition comprising the conjugate of claim 6 and a pharmaceutically acceptable additive.

8. A process for the preparation of a multi-arm single molecular weight polyethylene glycol according to claim 1, which comprises the step of reacting compound $A\text{-}(X_1\text{-}Y)_n$ with $W\text{-}X_2\text{-}PEG\text{-}PG$ to link them together, and the reaction formula is as follows:

$$A\text{-}(X_1\text{-}Y)_n + W\text{-}X_2\text{-}PEG\text{-}PG \rightarrow A\text{-}(X_1\text{-}R\text{-}X_2\text{-}PEG\text{-}PG)_n$$

wherein W is a terminal group selected from any one of the group consisting of: hydrogen, hydroxyl, carboxyl, ester group, ketone group, amino, mercapto group, maleimide group, alkynyl, and azido, and PG is a hydroxyl protecting group, A is a core structure, and is a polyol group selected from the group consisting of: residues of pentaerythritol, oligo-pentaerythritol, glycerol and oligoglycerol, and glyceryl ether groups thereof, $X_1$ is a linking group selected from any one or a combination of two or more of the group consisting of: $-(CH_2)_i-$, $-(CH_2)_iO-$, $-(CH_2)_iNHCO-$, $-(CH_2)_iCONH-$, $-(CH_2)_iOCO-$, and $-(CH_2)_iCOO-$, and i is an integer from 1 to 10, Y is a terminal group selected from any one of the group consisting of: hydrogen, hydroxyl, carboxyl, ester group, ketone group, amino, mercapto group, maleimide group, alkynyl, and azido, and n is an integer from 3 to 24.

* * * * *